(12) United States Patent  
Rader

(10) Patent No.: US 9,114,206 B2  
(45) Date of Patent: Aug. 25, 2015

(54) DEVICE FOR INFUSION OF PRESCRIPTION MEDICINES OR TREATMENTS

(75) Inventor: William K. Rader, Lake Havasu City, AZ (US)

(73) Assignee: RALAND TECHNOLOGIES, LLC, Rockville, MD (US)

( * ) Notice: Subject to any disclaimer, the term of this patent is extended or adjusted under 35 U.S.C. 154(b) by 884 days.

(21) Appl. No.: 12/765,415

(22) Filed: Apr. 22, 2010

(65) Prior Publication Data

US 2011/0264070 A1  Oct. 27, 2011

(51) Int. Cl.  
*A61M 5/00* (2006.01)  
*A61M 5/14* (2006.01)  
*A61M 39/22* (2006.01)

(52) U.S. Cl.  
CPC .......... *A61M 5/1408* (2013.01); *A61M 39/223* (2013.01)

(58) Field of Classification Search  
CPC . A61M 39/22; A61M 39/284; A61M 39/285; A61M 39/28; A61M 5/1408; A61M 39/223  
USPC ......... 604/151, 248, 246, 247, 110, 250, 258; 137/625.41, 556  
See application file for complete search history.

(56) References Cited

U.S. PATENT DOCUMENTS

| | | | |
|---|---|---|---|
| 3,411,534 A * | 11/1968 | Rose | 137/595 |
| 3,957,082 A * | 5/1976 | Fuson et al. | 137/625.41 |
| 4,559,036 A | 12/1985 | Wunsch | |
| 4,604,093 A * | 8/1986 | Brown et al. | 604/248 |
| 5,061,243 A | 10/1991 | Winchell et al. | |
| 5,439,452 A * | 8/1995 | McCarty | 604/248 |
| 6,126,642 A | 10/2000 | Kreisel et al. | |
| 7,488,309 B2 * | 2/2009 | Kissinger et al. | 604/246 |
| 7,905,865 B2 * | 3/2011 | Lee | 604/185 |
| 2005/0038387 A1 | 2/2005 | Kriesel et al. | |
| 2009/0012468 A1 | 1/2009 | Anderson et al. | |
| 2009/0137956 A1 | 5/2009 | Souter | |

OTHER PUBLICATIONS

International Search Report and Written Opinion in PCT/US2011/032953 dated Dec. 27, 2011.

* cited by examiner

*Primary Examiner* — Bhisma Mehta  
*Assistant Examiner* — Bradley G Thomas, Jr.  
(74) *Attorney, Agent, or Firm* — Duane Morris LLP

(57) ABSTRACT

An infusion assembly is provided having a first outlet conduit adapted to be in fluid communication with a delivery site of a patient. The assembly further includes at least first and second fluid inlet conduits adapted to be in fluid communication with at least a first and second fluid reservoir, and an infusion switching device, including a housing and an internal valve assembly. The internal valve assembly is adapted for selective manipulation by a patient or caregiver. The valve assembly includes an off-setting, and first infusion setting, for initiating an infusion of a first fluid from a first fluid reservoir to a delivery site, and a second infusion setting for initiating an infusion of a second fluid from a second fluid reservoir to a delivery site.

11 Claims, 4 Drawing Sheets

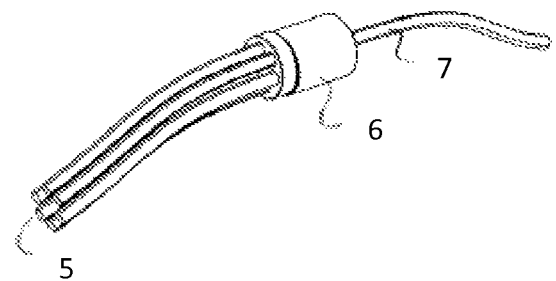
FIG. 6
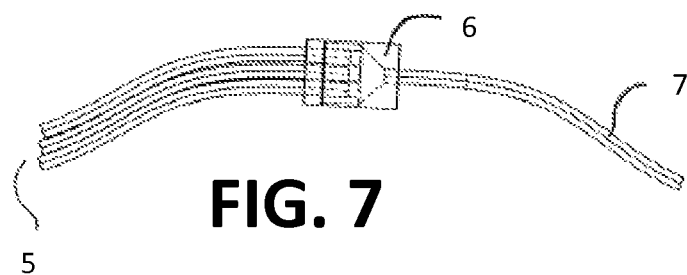
FIG. 7
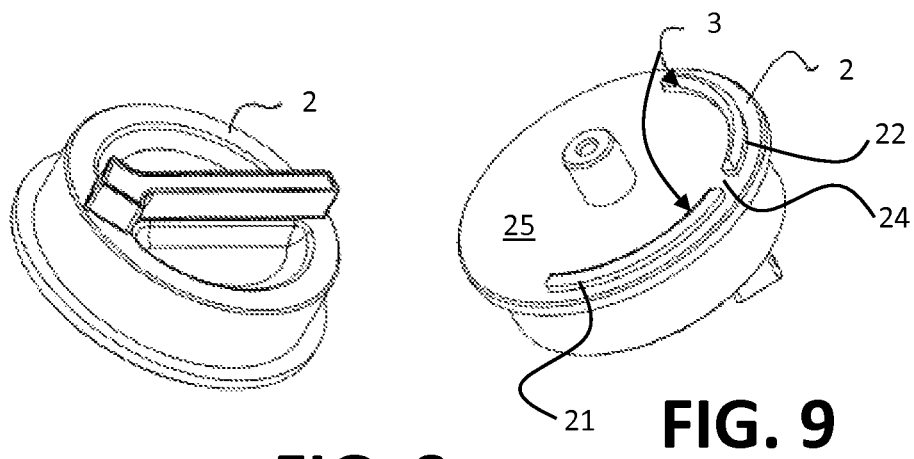
FIG. 8    FIG. 9

DEVICE FOR INFUSION OF PRESCRIPTION MEDICINES OR TREATMENTS

FIELD OF THE INVENTION

A medical device that allows for an easy and safer method for in-home drug infusion therapy.

BACKGROUND OF THE INVENTION

Intravenous ("IV") or infusion therapy is the administration of liquid substances directly into a vein. The word intravenous simply means "within a vein". Therapies administered intravenously are often called specialty pharmaceuticals.

Current infusion therapy and treatments are accomplished using a connection device that must be sterilized and connected between each medication, treatment or flush.

Not all infusion therapies are administered by healthcare professionals in a hospital setting. Many patients also self-infuse medications at home. In-home infusion of medications and therapies is accomplished by patients who may be afflicted by one or more of many diseases and afflictions. Home infusion therapies are presently available for the treatment of multiple sclerosis, hemophilia (factor therapy), parenteral and enteral nutrition, intravenous gamma globulin (IVIG), transplant and immunology therapies, anti-infectives, colony stimulating factors, inotropics, chemotherapy, pain management, IV fluids and antibiotics.

In particular, patients with multiple sclerosis are expected to self-infuse during times of disease "flair-ups" with limited or no medical supervision. Although not limited to this particular affliction, infusion therapy in an in-home treatment environment poses many challenges with poor sterility, adulteration of infused product and improper sequence of delivery of treatment. Such risks are potentially life threatening.

The current method of drug infusion involves manual switching of tubes and connectors with each infused product. Some of the infused products can look similar thus allowing for a mistake to be made in the infusion sequence. Further, the fact that it is necessary to connect, disconnect and sterilize each part in the connection process is tedious. If a person has any dexterity problems, these procedures can be difficult and cumbersome. There appears to be a need for a device which allows for a connection with simple hand operation allowing for decreased risk of adulteration of the infused product or incorrect sequence of infusion steps.

SUMMARY OF THE INVENTION

The present invention provides an infusion assembly, including a first outlet conduit adapted to be in fluid communication with a delivery site of a patient; at least first and second fluid inlet conduits adapted to be in fluid communication with at least a first and second fluid reservoir; an infusion switching device including a housing; and an internal valve assembly located in said housing, said internal valve assembly being adapted for selective manipulation by a patient or caregiver, said valve assembly having an off-setting, a first infusion setting, for initiating an infusion of a first fluid from a first fluid reservoir to said delivery site, and a second infusion setting for initiating an infusion of a second fluid from a second fluid reservoir to a delivery site.

The preferred assembly allows for a qualified or trained individual to fully prepare the complete home infusion therapy through a single switching device allowing for the decreased risk of error or additional steps. While in-home infusion therapy is currently accomplished using a connection device that must be sterilized and connected between each product being infused, the preferred device allows for a single connection with simple hand operation allowing for decreased risk of adulteration of the infused product or incorrect sequence of infusion steps.

With this invention, the patient, pharmacy, or a home health care worker would connect the appropriate medications or other injectables into the device's input connectors in the order in which they are to be administered. Once connected, the patient would switch to the first position to start the flow of injectable material or medication into their IV.

BRIEF DESCRIPTION OF THE DRAWINGS

The accompanying drawings illustrate preferred embodiments of the invention, as well as other information pertinent to the disclosure, in which:

FIG. 6 is a perspective view of a preferred manifold assembly of the infusion switching device of the present invention, including a plurality of input tubes and an output tube;

FIG. 7 is a perspective and phantom view of the manifold assembly of FIG. 6 showing the flow chambers within the manifold assembly;

FIG. 8 is a top and side perspective view of a preferred dial for the valve assembly; and FIG. 9 is a bottom and side perspective view of the dial of FIG. 8, showing a preferred valve cam structure.

DETAILED DESCRIPTION

Figure 1:
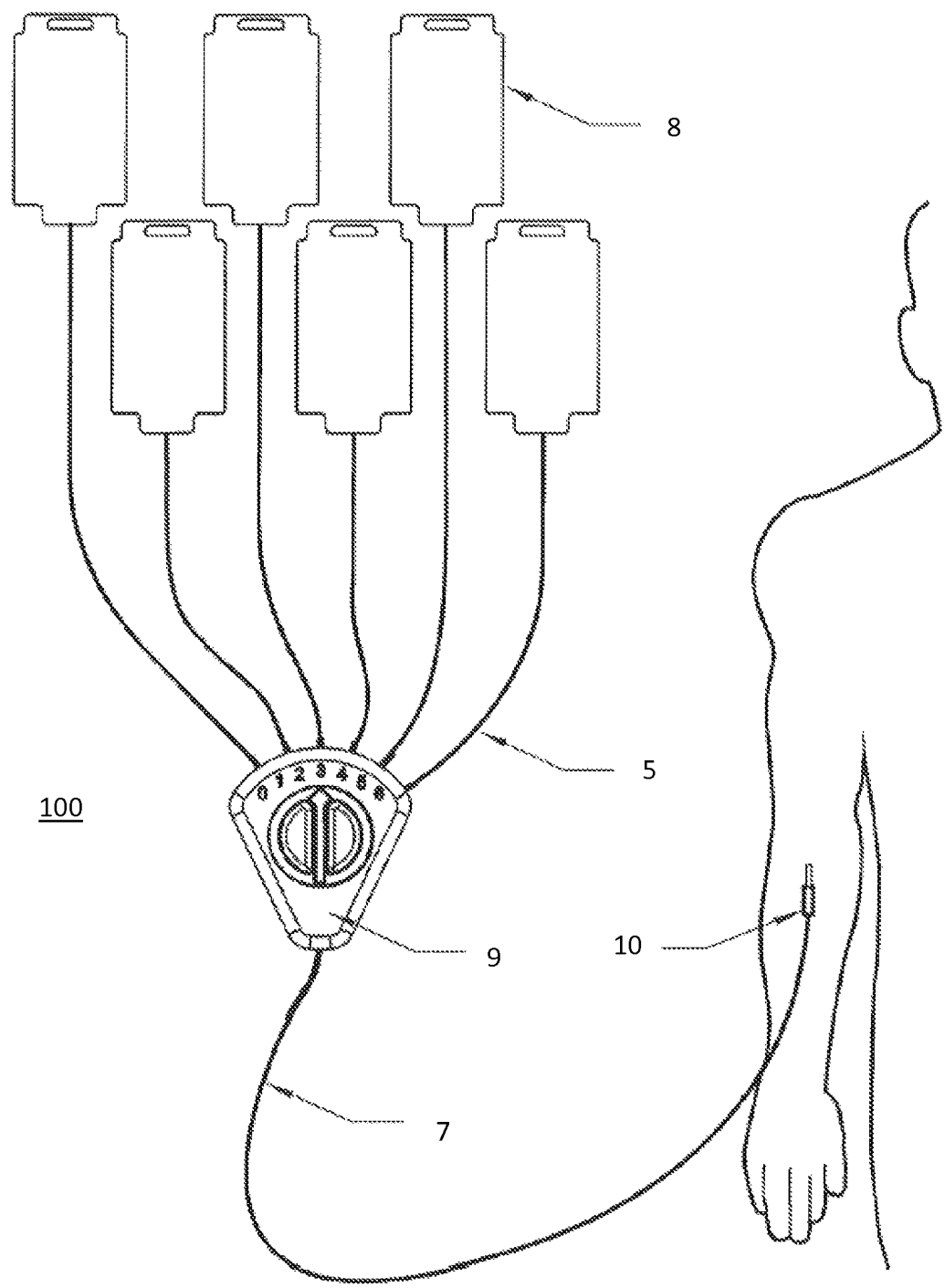
FIG. 1 is a partial front plan view of a patient being infused using the infusion switching device of the present invention.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. The term "distal" means further from the fluid reservoir, and "proximal" means closest to the fluid reservoir. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present invention helps to solve the problem of miss-administering multiple infused medications such as antibiotics, oncolytics, hormones, steroids, blood clotting agents, analgesics, that are provided in fluid or semi-solid form, via intravenous (IV) methods, and helps to reduce the chances of adulteration or contamination of an infused drug or other injectable product. As shown in the FIGS., and particularly in FIG. 1, the assembly 100 allows for a safe and controlled method for infusion of multiple drugs or treatment products intravenously. The assembly 100 includes an infusion switching device 9 disposed between the infused products and the patient, which assists in flushing and locking the lines using a single preferred switch method. The device allows for easy operation and self infusion by a patient, even in an in-home, non-medically supervised, environment. Currently in-home infusion therapy and treatments are accomplished using a connection device that must be sterilized and connected between each medication, treatment or flush. Such existing methods currently in use provide for a greater possibility of misapplication or improper sequence of infused medications, therapies or flush. The preferred assembly 100 allows for a connection with preferred simple hand operation allowing for decreased risk of adulteration of the infused product or incorrect sequence of infusion steps.

The present invention, illustrated in FIGS. 1-9, is an assembly 100 that provides for the multiple administration of infused medications via intravenous (IV) methods. In a preferred example, a plurality of fluid reservoirs 8 are connected to sterile input conduit or tubing 5 and disposed in select locations within an infusion switching device 9. A preferred single output conduit or tubing 7, which optionally can be more than one tube, is provided for attachment to a needle assembly 10, such as a needle or catheter.

Figure 2:
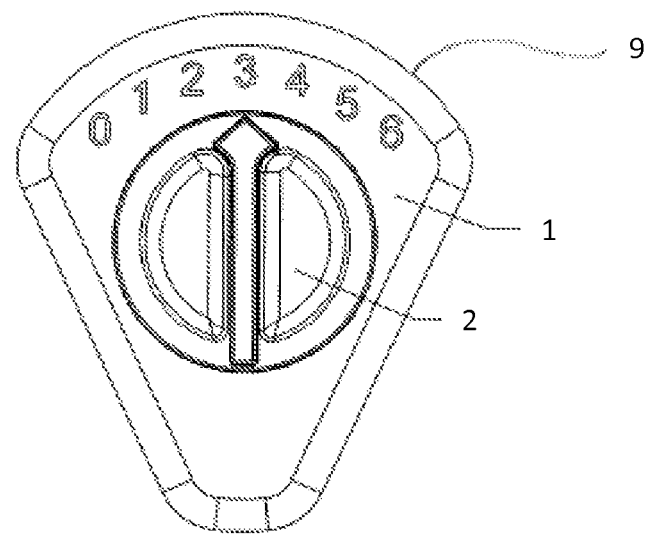
FIG. 2 is a top planar view of a preferred top enclosure of a housing for the preferred infusion switching device.
Figure 3:
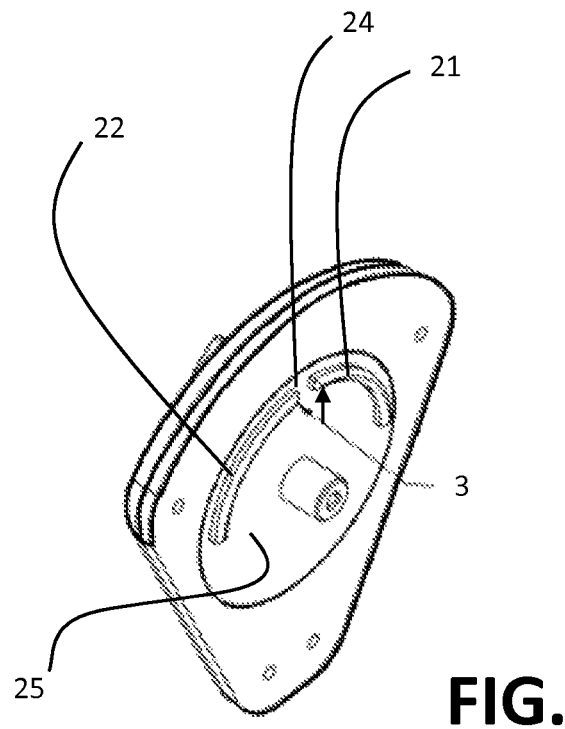
FIG. 3 is a front and side perspective view of the rear-facing surface of the top enclosure of FIG. 2.
Figure 4:
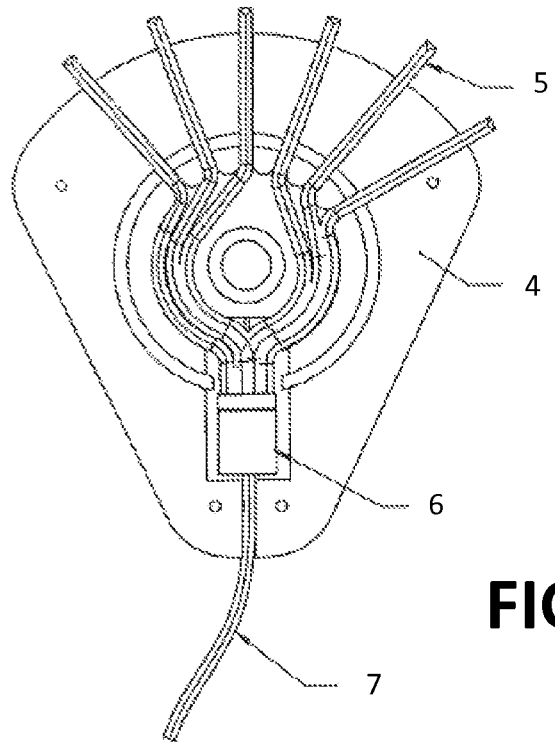
FIG. 4 is a top planar view of a preferred bottom enclosure of the housing of the infusion switching device of the present invention, showing input and output tubing.
Figure 5:
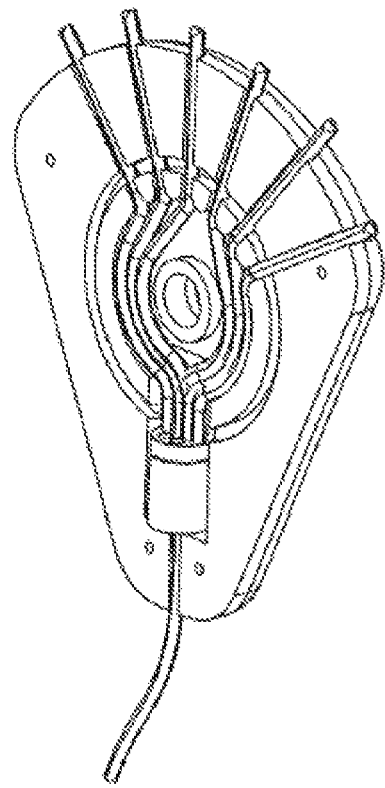
FIG. 5 is a front and side perspective view of the bottom enclosure of FIG. 4.

As shown in FIG. 2, the infusion switching device comprises a housing including a top enclosure 1, a valve dial 2, and as shown in FIG. 3, a valve cam 3. Generally, the housing includes a fluid outlet conduit or tubing 7 adapted to be in fluid communication with a delivery site of a patient, such as a needle assembly 10. The assembly 100 also includes at least first and second fluid inlet conduits or tubing 5 adapted to be in fluid communication with at least first and second fluid reservoirs 8. In the preferred embodiment, the input tubing 5 is disposed continuously through the bottom enclosure 4, as shown in FIG. 4. The ends of the input tubing 5 are disposed into a manifold assembly 6 having an input ferrule portion having at least a first receiving connector or aperture for attachment of the first input tube for receiving a first fluid, and a second receiving connector or aperture for attachment of a second input tube for receiving a second fluid. The manifold assembly 6 further includes an output ferrule portion having at least a first receiving connector or aperture for attachment of a first output tube 7. The connection of the input tubing 5 and the output tubing 7 by way of the manifold assembly 6 is described in FIG. 4-6. It is also possible for the input tubing 5 and output tubing 7 to be connected to the manifold assembly 6 by male connections extending from the manifold assembly 6, instead of being inserted into apertures.

In a preferred embodiment, the input tubing 5 and output tubing 7 are attached (either permanently or temporarily) to the manifold 6, prior to use by the patient. The tubing and manifold 6 would be sterile or made sterile. Preferably, only these portions of the assembly 100 would come in contact with any infusion product. This will allow for the input tubing 5, manifold assembly 6, and output tubing 7 to be disposable, allowing for the housing, including its top and bottom enclosures 1 and 4, to be reusable. In this way, a specialty pharmacy or the like, could assemble the assembly 100 as a whole, with all proper medication set up in the correct order. A patient would receive the assembly 100 fully set up, or add the infusion switching device 9, before treatment begins. At the end of the treatment cycle, the patient could, if they choose, return the device for a core change rebate, as the top and bottom closures 1 and 4 could be reused after sterilization or other sanitary considerations. The manifold assembly 6 and tubing could be disposable, removing the risk of cross contamination and allowing the re-use of the infusing switching device 9. Alternatively, the switching device 9 could be made of inexpensive plastic components and could also be disposable.

As shown in FIG. 2, the preferred top enclosure 1 includes a valve dial 2 on an exterior surface of the top enclosure 1 of the infusion switch device 9, and a valve cam 3 located on the inside surface of the top enclosure 1, as shown in FIG. 3. While the selector in the valve dial 2 is in the "0" or "off" position, a seal will be provided such that none of the input tubes of the input tubing 5 will fluidly connect with the output tubing 7, through the manifold assembly 6. When the selector of the valve dial 2 is positioned at locations "1" through "6", the groove forming a gap in the cam 3 will rest over a select one of tubes of the input tubing 5 to release product from one of the fluid reservoirs 8 through the manifold assembly 6 and into the output tubing 7, so that it can be infused through the needle assembly 10 into the patient. Preferably, the selector is manually adjusted from positions "0" through "6", consecutively, by the patient for the time selected for each infusion step. The valve dial 2 can be disposed to rotate either clockwise or counterclockwise, or both. Preferably, the valve dial 2 comprises a reverse motion stop to prevent manipulation of the device to a previously used position during treatment. In a preferred embodiment of infusion device 9, the housing is provided with a valve assembly. The valve assembly is adapted for selective manipulation by a patient, for example, the infusion valve assembly can include an off-setting (settings shown as numerals 0-6 in FIG. 2); a first infusion setting, for initiating an infusion of a first fluid from the first fluid reservoir through the first input conduit to said delivery site and a second infusion setting, for initiating an infusion of a second fluid from said second fluid reservoir through the second inlet conduit to said delivery site. The internal valve assembly has a valve cam 3, this value cam 3 has a circular planar portion 25 (which can be the back of the dial 2, as shown in FIGS. 3 and 9), and further includes first and second arcuate cam surface portions 21 and 22, each of said arcuate cam surface portions 21 and 22 having a longitudinal length and first and second ends and a raised surface extending from said planar portion 25 (shown in FIGS. 3 and 9). The first and second arcuate cam surface portions 21 and 22 are separated by a gap 24 (also shown in FIGS. 3 and 9), said gap 24 being located between a first end of said first arcuate cam surface 21 portion and a second end of said second arcuate cam surface portion 22. The dial 2 of the valve assembly can be rotatable to at least a first and a second infusion setting, wherein when set in the first infusion setting said gap 24 is aligned with said first fluid inlet conduit, which prevents the first fluid inlet conduit from being pinched closed by the valve cam, while pinching closed the second fluid inlet conduit, wherein when set to the first fluid inlet conduit is selected for conveying a corresponding infusion fluid to the output conduit space (such as by moving the dial from the 2 to the 1 position or from the 0 to the 1 position, for example). The dial 2 can then be rotated to a second infusion setting, wherein the gap 24 is aligned with the second fluid inlet conduit, which prevents the second fluid inlet conduit from being pinched closed by the valve cam, while pinching closed the first fluid inlet conduit, wherein the second fluid inlet conduit is selected for conveying a corresponding infusion fluid to the output conduit (such as by moving the dial from the 1 to the 2 position, for example).

In addition, it may be desirable to provide a control valve, such as a pincher valve, on or near the bottom of the infusion switching device 9 that would provide for a roughly calibrated flow rate of product to the patient. For example, a small rotating pincher valve that would clamp down on the output tubing 7, allowing for a reduced flow rate of the product. It desirably could provide a rough indication of flow, such as a dial indicator, allowing for limiting the rate should a standard flow limiter not be provided on the product itself.

Alternatively, the present device could provide an infusion switching device that has internal tubes with male or female connectors for attaching to externally applied input tubing 5 or output tubing 7. The internal tubes could be chambers or conduits of any fluid tight variety. Infusion switching device 9 could also be equipped with electronic flow meters and digital displays. Such displayed information could include the identity of the infusion products taken, the amount, rate, and order of sequencing, or whether there was a mistake in the administration of infusion products, etc. This information could be electronically transmitted to a healthcare professional, such as a primary care physician, via telephonic, cellular or web based communication systems attached to the device, or connected via a local area network, for example.

Although the invention has been described in terms of exemplary embodiments, it is not limited thereto. Rather, the appended claims should be construed broadly to include other variants and embodiments of the invention that may be made by those skilled in the art without departing from the scope and range of equivalents of the invention.

What is claimed:

1. An infusion assembly comprising:
  (a) a manifold assembly having a fluid outlet conduit adapted to be in fluid communication with a delivery site of a patient, said manifold assembly having at least first and second fluid inlet conduits in selective fluid communication with the fluid outlet conduit, said first and second fluid inlet conduits adapted to be in fluid communication with at least a first and a second fluid reservoir; and
  (b) an infusion switching device separate from the manifold assembly and said conduits, said infusion switching device including a housing and an internal valve assembly located within said housing, said internal valve assembly being adapted for selective manipulation by a patient, said infusion valve assembly having an off-setting; a first infusion setting, for initiating an infusion of a first fluid from said first fluid reservoir through the first fluid inlet conduit to said delivery site; and a second infusion setting, for initiating an infusion of a second fluid from said second fluid reservoir through the second fluid inlet conduit to said delivery site, said internal valve assembly having a valve cam, said valve cam, said value cam having a circular planar portion and first and second arcuate cam surface portions, each of said arcuate cam surface portions having a longitudinal length and first and second ends and a raised surface extending from said planar portion, said first and second arcuate cam surface portions separated by a gap, said gap being located between a first end of said first arcuate cam surface portion and a second end of said second arcuate cam surface portion; and
  (c) the valve assembly being rotatable to at least a first and a second infusion setting,
    wherein when set to the first infusion setting, said gap is aligned with said first fluid inlet conduit, which prevents the first fluid inlet conduit from being pinched closed by the valve cam, while pinching closed the second fluid inlet conduit, wherein the first fluid inlet conduit is selected for conveying a corresponding infusion fluid to the fluid outlet conduit, and
    wherein when set to the second infusion setting, said gap is aligned with said second fluid inlet conduit, which prevents the second fluid inlet conduit from being pinched closed by the valve cam, while pinching closed the first fluid inlet conduit, wherein the second fluid inlet conduit is selected for conveying a corresponding infusion fluid to the fluid outlet conduit.

2. The infusion assembly of claim 1, wherein the valve assembly is rotatable to align the gap with each of the fluid inlet conduits in sequence, for conveying the respective infusion fluids to the fluid outlet conduit in a corresponding sequence.

3. The infusion assembly of claim 1, wherein the valve assembly is rotatable to an off position, wherein the valve cam pinches closed all respective fluid inlet conduits while the respective fluid input conduits remain continuously connected to the fluid outlet conduit, and wherein the gap is aligned with none of the respective fluid input conduits.

4. The infusion assembly of claim 1, wherein the housing comprises a bottom enclosure and a top enclosure, wherein the bottom closure receives the manifold assembly and respective portions of the fluid outlet conduit and input inlet conduits, and the top enclosure receives the valve assembly for rotation on the housing.

5. The infusion assembly of claim 1, wherein the manifold assembly, the fluid outlet conduit and the fluid inlet conduits comprise an assembly separate from the infusion switching device, and the housing and the rotatable valve dial are removably assembled onto the one assembly.

6. The infusion assembly of claim 1, comprising:
  a plurality of fluid reservoirs containing the respective infusion fluids, wherein the fluid reservoirs are connected to respective fluid inlet conduits for supplying the respective infusion fluid to the respective fluid inlet conduits.

7. The infusion assembly of claim 1, wherein the manifold assembly, the fluid outlet conduit and the fluid inlet conduits comprise an assembly separate from the infusion switching device, and further comprising, a plurality of fluid reservoirs containing the respective infusion fluids being connected to respective fluid inlet conduits.

8. The infusion assembly of claim 7, wherein the valve assembly is rotatable to align the gap with each of the fluid inlet conduits in sequence, for conveying the respective infusion fluids to the fluid outlet conduit in a corresponding sequence.

9. The infusion assembly of claim 7, wherein the valve assembly is rotatable to an off position, wherein the valve cam pinches closed all respective fluid inlet conduits while the respective fluid inlet conduits remain continuously connected to the fluid outlet conduit, and wherein the gap is aligned with none of the respective fluid inlet conduits.

10. The infusion assembly of claim 7, wherein the housing comprises a bottom enclosure and a top enclosure, wherein the bottom closure receives the manifold assembly and respective portions of the fluid outlet conduit and the fluid inlet conduits, and the top enclosure receives the valve assembly for rotation on the housing.

11. The infusion assembly of claim 1, wherein by said gap is sized to permit the flow of the first fluid or the second fluid, but not both at once.

* * * * *